US010081605B2

(12) United States Patent
Cantrell, Jr. et al.

(10) Patent No.: US 10,081,605 B2
(45) Date of Patent: Sep. 25, 2018

(54) SYNTHESIS OF CYCLOCREATINE AND ANALOGS THEREOF

(71) Applicant: Lumos Pharma, Inc., Austin, TX (US)

(72) Inventors: William R. Cantrell, Jr., San Anotnio, TX (US); William E. Bauta, San Anotnio, TX (US)

(73) Assignee: Lumos Pharma, Inc., Austin, TX (US)

( * ) Notice: Subject to any disclaimer, the term of this patent is extended or adjusted under 35 U.S.C. 154(b) by 0 days.

(21) Appl. No.: 15/556,657

(22) PCT Filed: Mar. 11, 2016

(86) PCT No.: PCT/US2016/021947
§ 371 (c)(1),
(2) Date: Sep. 8, 2017

(87) PCT Pub. No.: WO2016/145286
PCT Pub. Date: Sep. 15, 2016

(65) Prior Publication Data
US 2018/0044299 A1      Feb. 15, 2018

Related U.S. Application Data

(60) Provisional application No. 62/131,321, filed on Mar. 11, 2015.

(51) Int. Cl.
| C07C 61/08 | (2006.01) |
| C07C 61/10 | (2006.01) |
| C07C 229/00 | (2006.01) |
| C07C 315/00 | (2006.01) |
| C07C 317/00 | (2006.01) |
| C07C 321/00 | (2006.01) |
| C07C 323/00 | (2006.01) |
| C07C 381/00 | (2006.01) |
| C07D 239/14 | (2006.01) |
| C07C 277/02 | (2006.01) |
| C07C 279/14 | (2006.01) |
| C07C 279/12 | (2006.01) |

(52) U.S. Cl.
CPC .......... *C07D 239/14* (2013.01); *C07C 277/02* (2013.01); *C07C 279/12* (2013.01); *C07C 279/14* (2013.01)

(58) Field of Classification Search
CPC .................................................. C07C 229/02

USPC .......................................................... 562/507
See application file for complete search history.

(56) References Cited

U.S. PATENT DOCUMENTS

| 5,321,030 A | 6/1994 | Kaddurah-Daouk et al. |
| 7,834,144 B2 | 11/2010 | Peretz et al. |
| 2008/0242639 A1 | 10/2008 | Ahmed et al. |
| 2010/0303840 A1 | 12/2010 | Kaddurah-Daouk et al. |

FOREIGN PATENT DOCUMENTS

| CN | 103923014 A | 7/2014 |
| WO | 9312781 A2 | 7/1993 |
| WO | 2014204763 A1 | 12/2014 |

OTHER PUBLICATIONS

The extended European search report, dated Jan. 3, 2018, in the related European Appl. No. 15837263.1.
Smejkal et al., "Transition-State Stabilization by a Secondary Substrate-Ligand Interaction: A New Design Principle for Highly Efficient Transition-Metal Catalysis," Chemistry—A European Journal, vol. 16, 2010, pp. 2470-2478.
The International Search Report and Written Opinion, dated May 23, 2016, in the corresponding PCT Appl. No. PCT/US16/21947.
The International Search Report and Written Opinion, dated Dec. 4, 2015, in the related PCT Appl. No. PCT/PCT/US15/47880.
Rowley, GL et al. "On the Specificity of Creatine Kinase. New Glycocyamines and Glycocyamine Analogs Related to Creatine," Journal of the American Chemical Society, vol. 93, No. 21, Oct. 20, 1971, pp. 5542-5551; p. 5545, chart 1.
The US Office Actions, dated Jul. 26, 2017 and Apr. 2018, respectively, in the related U.S. Appl. No. 15/506,014.

*Primary Examiner* — Jeffrey H Murray

(57) ABSTRACT

Provided herein is a process and intermediates for the preparation of a compound of formula (I):

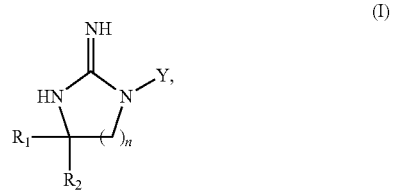

or a pharmaceutically acceptable salt thereof, using cyanamide in the reaction.

2 Claims, No Drawings

SYNTHESIS OF CYCLOCREATINE AND ANALOGS THEREOF

CROSS-REFERENCE TO RELATED APPLICATIONS

This application is a National Stage Application of PCT/US2016/021947 filed Mar. 11, 2016, which claims priority from U.S. Provisional Patent Application No. 62/131,321, filed on Mar. 11, 2015. The priority of both said PCT and U.S. Provisional Patent Application are claimed. Each of prior mentioned applications is hereby incorporated by reference herein in its entirety.

FIELD OF THE INVENTION

The invention relates to a chemical process and intermediates for the preparation of cyclocreatine and related cyclic creatine analogs with application in the treatment of creatine transporter deficiency.

All documents cited or relied upon below are expressly incorporated herein by reference.

BACKGROUND OF THE INVENTION

Cyclocreatine ((2-iminoimidazolidin-1-yl)acetic acid) is used in the treatment of creatine transporter defect. In this genetic disease, a mutation affects the creatine transporter thereby preventing creatine from crossing the blood-brain barrier (BBB), leading to a deficiency of this important amino acid in the brain. Creatine is a polar small molecule and requires active transport to cross the BBB. By contrast, cyclocreatine is more lipophilic owing to its two additional methylene groups and is able to cross the BBB by passive diffusion, thereby functioning as a creatine surrogate.

The synthesis of cyclocreatine was first reported in Rowley, G. L.; Greenleaf, A. L.; Kenyon, G. L. *J. Am. Chem. Soc.* 1971, 93, 5542-5551. The synthesis and characterization of cyclocreatine salts with pharmaceutically acceptable acids was later described in WO 2006/073923. The Rowley synthesis of cyclocreatine starts from the sodium salt of N-carboxymethyl-1,2-diaminoethane. This intermediate is maintained in solution and reacted with a methanolic solution of cyanogen bromide to afford the crude product, which is isolated by filtration from the reaction mixture. Final recrystallization is performed from water to afford the purified product.

The Rowley synthesis, however, is limited by poor overall yield. Further, the use of cyanogen bromide, a highly toxic and reactive compound, requires significant engineering controls for use on scale. More specifically, cyanogen bromide is a low-melting solid with a significant vapor pressure (mp=50-53° C., bp=61-62° C.) and is toxic by inhalation, dermal exposure, and oral ingestion. Indeed, plasma levels of 2.5 μg/mL cause convulsions and death in mice.

A need exists in the art, therefore, for a new synthesis of cyclocreatine and analogs thereof that is less toxic and provides for products in greater yield and at a lower commercial cost.

SUMMARY OF THE INVENTION

The present invention is directed to a process for the preparation of a compound of formula (I):

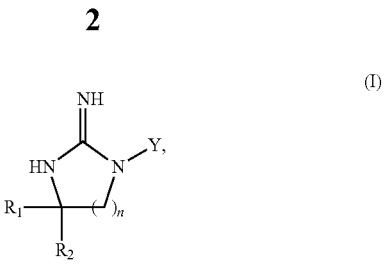

or a pharmaceutically acceptable salt thereof, comprising the step of reacting a compound of formula (II):

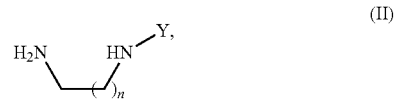

with a compound of formula (III):

wherein:
Y is $CH_2CO_2H$, $CH_2CONR_1R_2$ or $CH_2CO_2R_1$;
$R_1$, $R_2$, independently of each other, is hydrogen, lower alkyl, $C_7$-$C_{12}$ alkyl or lower cycloalkyl; and
n is 1, 2, 3, 4 or 5.

DETAILED DESCRIPTION

The present invention is directed at an improved synthetic method for making cyclocreatine, and intermediates and other cyclic creatine analogs, in greater overall yield and with improved safety. Cyanamide is a readily available commodity chemical and is significantly less toxic than cyanogen bromide.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

The following definitions are used in connection with the invention:

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

"Lower alkyl" or "$C_1$-$C_6$ alkyl" refers to a straight or branched chain saturated hydrocarbon containing 1-6 carbon atoms. Examples of a lower alkyl group include, but are not limited to, methyl, ethyl, propyl, butyl, pentyl, hexyl, isopropyl, isobutyl, sec-butyl, tert-butyl, isopentyl, and neopentyl.

"$C_7$-$C_{12}$ alkyl" refers to a straight or branched chain saturated hydrocarbon containing 7-12 carbon atoms.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

It is understood that any of the substitutable hydrogens on a lower alkyl, $C_7$-$C_{12}$ alkyl or cycloalkyl can be substituted independently with one or more substituents, for example 1, 2 or 3 substituents. Examples of substituents include, but are not limited to, halogen, $C_1$-$C_3$ alkyl, hydroxyl, alkoxy, oxo and cyano groups.

A "patient" is a mammal, e.g., a human, mouse, rat, guinea pig, dog, cat, horse, cow, pig, or non-human primate, such as a monkey, chimpanzee, baboon or rhesus monkey, and the terms "patient" and "subject" are used interchangeably herein.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. Additional pharmaceutically acceptable salt forms at the carboxylate function would include lithium, sodium, and potassium.

A "therapeutically effective amount" when used in connection with cyclocreatine is an amount effective for treating or preventing a cyclocreatine-regulated disease or disorder.

It will be understood by those skilled in the art that the compounds recited herein and in the appended claims can be present in the form of zwitterions, enantiomers, mixtures of enantiomers such as, for example, racemates, mixtures of diastereoisomers, diastereoisomeric racemates or mixtures of diastereoisomeric racemates.

It will also be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmacologically relevant half-life at physiological conditions.

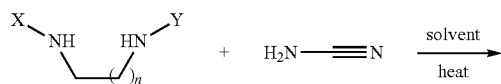

1

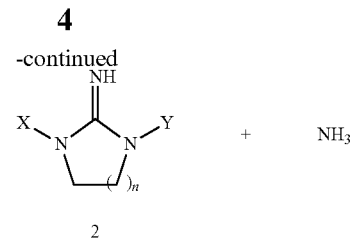

2

As seen in Scheme I above, the present invention describes a method for the preparation of various cyclic analogs of creatine (2) by the condensation of diamines or their salts (1) with cyanamide in a suitable solvent to afford 7 and ammonia or a salt thereof. In one embodiment of the invention, 1 (X=H, Y=$CH_2CO_2H$, n=1) is reacted with cyanamide in ethanol or water at 25-100° C. to afford 2 (X=H, Y=$CH_2CO_2H$, n=1). The diamine may be a purified substance or a mixture containing approximately 20-99% 6. The product 2 may, in some embodiments, be further purified by crystallization or slurry from water or another suitable solvent to afford 7 in ≥97% chemical purity. Alternate embodiments of 2 can include compounds of formula:

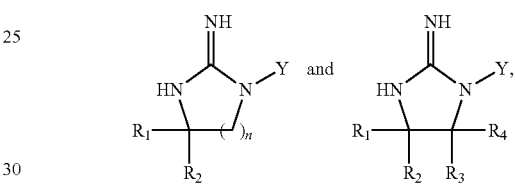

wherein $R_1$, $R_2$, $R_3$, $R_4$, independently of each other, can be hydrogen, lower alkyl or cycloalkyl, or a pharmaceutically acceptable salt thereof.

Thus, in one embodiment, provided is a process for the preparation of a compound of formula (I):

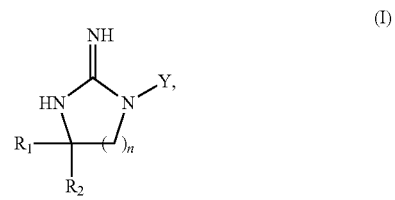

(I)

or a pharmaceutically acceptable salt thereof, comprising the step of reacting a compound of formula (II):

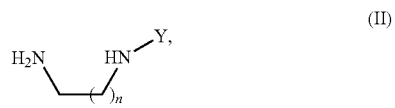

(II)

with a compound of formula (III):

(III)

wherein:
Y is $CH_2CO_2H$, $CH_2CONR_1R_2$ or $CH_2CO_2R_1$;
$R_1$, $R_2$, independently of each other, is hydrogen, lower alkyl, $C_7$-$C_{12}$ alkyl or lower cycloalkyl; and
n is 1, 2, 3, 4 or 5.

In another embodiment of the present invention, provided is a process for the preparation of a compound of formula (I), wherein a carbon within the parentheses in the compound of formula (I) is optionally substituted with $R_3$ and $R_4$, each of which independently of each other is hydrogen, lower alkyl or cycloalkyl.

In another embodiment of the present invention, provided is a process for the preparation of a compound of formula (I), wherein n is 1.

In another embodiment of the present invention, provided is a process for the preparation of a compound of formula (I), wherein the compound of formula (I) is cyclocreatine or a pharmaceutically acceptable salt thereof.

In another embodiment of the present invention, provided is a process for the preparation of a compound of formula (I), wherein said compound is a compound of formula (Ia):

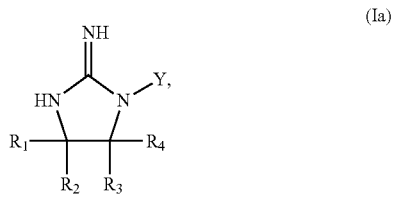

wherein:
Y is $CH_2CO_2H$, $CH_2CONR_1R_2$ or $CH_2CO_2R_1$;
$R_1$, $R_2$, $R_3$, $R_4$, independently of each other, is hydrogen, lower alkyl, $C_7$-$C_{12}$ alkyl or cycloalkyl,
or a pharmaceutically acceptable salt thereof.

In another embodiment of the present invention, provided is a process for the preparation of a compound of formula (I), further comprising a precursor step of reacting ethylenediamine with chloroacetic acid to produce said compound of formula (II).

In another embodiment of the present invention, provided is a process for the preparation of a compound of formula (I), wherein the concentration of cyanamide is 1-20 molar equivalents relative to a molar charge of chloroacetic acid.

Intermediates A and B

It was discovered that intermediates are formed during the reaction of the compound of formula (II) and cyanamide when forming cyclocreatine. These intermediates include the compound of formula A ([(2-carbamimidamidoethyl)amino]acetic acid A):

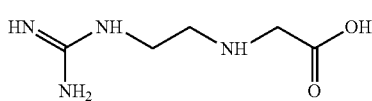

and the structurally isomeric intermediate [N-(2-aminoethyl)carbamimidamido]acetic acid B:

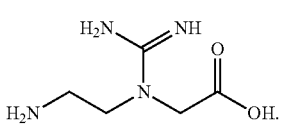

Intermediate A can be formed by the following process: Chloroacetic acid (3) can be reacted with ten molar equivalents of ethylenediame (4) in DMSO at 5-10° C. for 7.5 h and the reaction mixture can be distilled under reduced pressure to remove most of the ethylene diamine. The resultant crude residue can be treated with DMSO and filtered to afford crude [(2-Aminoethyl)amino]acetic acid (3). This can be washed with isopropanol and MTBE and dried under vacuum to produce 3 in 88% isolated yield. Product 3 can then be reacted in water by addition of an aqueous solution of cyanamide (one molar equivalent) and heating from 22° C. to 84° C. The resultant cyclocreatine solid that forms in solution can be filtered and subsequently slurried in water at ambient temperature. In one embodiment, the cyclocreatine was filtered and dried under vacuum with an isolated yield of 43%. It was observed that Intermediate A is a chemical composition that forms during the preparation of cyclocreatine from 3 and cyanamide. This intermediate can further react to form cyclocreatine. Intermediate A, as well as isomeric form B, can be useful in the preparation of cyclocreatine such that a solution of either intermediate may react in a suitable solvent, such as water, to form cyclocreatine at room temperature or elevated temperatures such as 40-80° C.

Thus, in another embodiment of the present invention, provided is a compound, selected from the group consisting of:

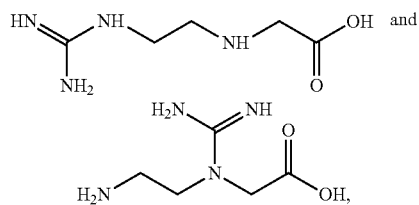

or a pharmaceutically acceptable salt thereof.

In a further embodiment of the present invention, provided is a process for making a compound of formula (A):

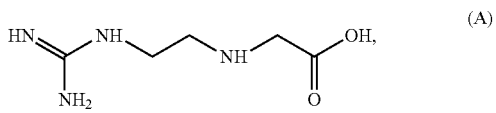 [SMILES: N=C(N)NCCNCC(=O)O]

comprising the steps of:
reacting a compound of formula 3 or a salt thereof:

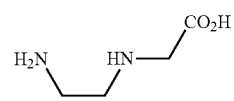

with a compound of formula (III):

In an additional embodiment of the present invention, provided is a process for making cyclocreatine or a pharmaceutically acceptable salt thereof, comprising the step of reacting a compound of formula (A):

with a compound of formula (A):

$$HN=C(NH_2)-NH-CH_2CH_2-NH-CH_2-C(O)-OH \quad (A)$$

with a compound of formula (III):

$$H_2N-C\equiv N. \quad (III)$$

In a still further embodiment of the present invention, provided is a process for making cyclocreatine or a pharmaceutically acceptable salt thereof, comprising the step of reacting a compound of formula (B):

$$H_2N-CH_2CH_2-N(C(=NH)NH_2)-CH_2-C(O)-OH \quad (B)$$

with a compound of formula (III):

$$H_2N-C\equiv N. \quad (III)$$

In another embodiment of the present invention, provided is cyclocreatine, or a pharmaceutically acceptable salt thereof, prepared by a process comprising the step of reacting a compound of formula (A):

$$HN=C(NH_2)-NH-CH_2CH_2-NH-CH_2-C(O)-OH \quad (A)$$

or a compound of formula (B):

$$H_2N-CH_2CH_2-N(C(=NH)NH_2)-CH_2-C(O)-OH \quad (B)$$

with a compound of formula (III):

$$H_2N-C\equiv N. \quad (III)$$

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Preparation of Intermediate 3 in MTBE $$H_2N-CH_2CH_2-NH_2 + Cl-CH_2-CO_2H \xrightarrow{\text{MTBE}, 22°C} H_2N-CH_2CH_2-NH-CH_2-CO_2H \quad (3)$$

A 500 mL flask was charged with ethylenediamine (62.03 g, 1032 mmol). A solution of chloroacetic acid (6.502 g, 68.80 mmol) in tert-butyl methyl ether (MTBE, 30 mL) was added with magnetic stirring at 22° C. over 0.5 h. The internal temperature had risen to 41° C. during the addition. After stirring an additional 40 min, toluene (100 mL) was added and the mixture concentrated by rotary evaporation; this procedure was done twice more and the resultant residue further dried under high vacuum to afford 16.4 g crude product. The product composition, as evaluated by HPLC/MS was 3 (37.3%), and the corresponding diacid (62.7%).

Example 1a

Preparation of Intermediate 3 in MTBE Via Solvent Extraction Method

To a cooled (5-10° C.) and stirred solution of ethylenediamine (420 mL, 6.36 mol) in MTBE (800 mL) was added a solution of chloroacetic acid (60.0 g, 0.63 mol) in MTBE (400 mL plus 100 mL heel) over 2-3 h under nitrogen. After the addition, the reaction mixture was stirred at 5-10° C. for 0.5 h, then slowly warmed to room temperature and stirred for 18 h. The top clear layer was removed via suction, and the bottom viscous layer was washed twice with MTBE (2×600 mL), again suctioning the top layer each time. DMSO (300 mL) was added and the reaction mixture stirred at room temperature for 0.5 h. To the reaction mixture 2-propanol (300 mL) was added and stirred at room temperature for 18 h. The milky, opaque solution formed a white precipitate within 3 h at room temperature. The reaction mixture was cooled to 10-15° C. and held for 0.5 h. The white precipitate was filtered, washed twice with IPA (2×150 mL), then twice with MTBE (2×150 mL), dried under vacuum at room temperature for 18 h to afford a 50.8 g crude product. $^1$H NMR confirmed the structure as intermediate 3.

Example 2

Preparation of Intermediate 3 in Toluene $$H_2N-CH_2CH_2-NH_2 + Cl-CH_2-CO_2H \xrightarrow{\text{PhMe}, 70°C}$$

-continued

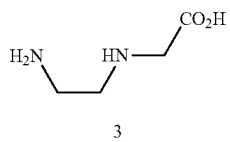

3

A 40 mL vial with a stopper and magnetic stir bar was charged with ethylenediamine (9.2 g, 153.7 mmol). A syringe pump was charged with a solution of chloroacetic acid (0.968 g, 10.24 mmol) in PhMe (total volume 9.5 mL). The syringe pump was set to deliver at a rate of 19.0 ml/h. The vial containing the ethylenediamine was heated in an aluminum heating block to 70° C. and the addition initiated at this time. After the addition was complete (~30 min), the vial was removed from the heating block and cooled to room temperature. The supernatant layer of liquid was removed by pipette and the remainder evaporated under high vacuum. HPLC/MS analysis of the residue revealed 92.8% mono-acid 3 and 7.2% diacid.

Example 3

Preparation of Cyclocreatine from 3 and Cyanamide

A portion of the crude batch of 3 described in Example 1 (5.32 g) was charged to a 100 mL round bottom flask with a stir bar as a solution in $H_2O$ (7.6 mL). Solid cyanamide (1.447 g, 34.41 mmol) was charged as a solid and the flask fitted with a reflux condenser and placed in a 70° C. oil bath. After stirring 20 h, the mixture was cooled to room temperature and the solid filtered, washed with $H_2O$ (2 mL) and dried under high vacuum to afford crude cyclocreatine (1.161 g, ~23.5% yield). HPLC/MS analysis of this solid revealed 99.3% of cyclocreatine, 0.7% of monoacid 3, and none of the diacid. The crude product (1.009 g) was charged to a vial and $H_2O$ (4.147 g) added. The mixture was heated to boiling but this did not result in complete dissolution of the solid. An additional charge of $H_2O$ (3.643 g) with continued heating led to complete dissolution (7.1 mL/g water added for dissolution). The mixture was cooled after 3 h heating and the resultant solid filtered and washed with $H_2O$ (2 mL). Drying under vacuum afforded pure cyclocreatine (0.498 g, 10.1% yield).

Example 4

Preparation of Cyclocreatine Via Reaction with Cyanamide

A 250 mL flask, equipped with mechanical stirrer, was charged with ethylenediamine (28.08 g, 467.3 mmol) and the flask was heated to 70° C. A solution of chloroacetic acid (2.944 g, 31.15 mmol) in toluene (28 mL) was added to the reaction over 30 minutes. The mixture was cooled to ambient temperature and stirring was stopped. The top layer containing toluene and ethylenediamine was removed. Toluene (15 mL) was added to the reaction and the mixture was stirred. Stirring was stopped and the top layer was removed. Toluene (15 mL) was added and the reaction mixture was concentrated. Isopropanol (30 mL) was added and the mixture was cooled to <0° C. and held for 3 days. The reaction mixture was concentrated and ethanol (20 mL) was added. The resulting slurry was filtered and the flask and solids were washed with ethanol. The solids were dried by high vacuum to give 3 (1.286 g, 27%) $^1$H NMR (400 MHz, $D_2O$) δ 3.32 (s, 2H), 3.07 (t, 2H, J=6 Hz), 2.95 (t, 2H, J=6 Hz). None of the di-acid isomers were detected by NMR. A 40 mL vial with magnetic stir bar was charged with compound 3 (1.224 g, 7.918 mmol) and water (8.7 mL). Cyanamide (0.333 g, 7.918 mmol) was added as a solid. The mixture was heated to 70° C. and stirred for 3.5 hours. Analysis by LCMS showed 57% conversion. More cyanamide (0.266 g, 6.327 mmol) was added and the mixture was stirred at 70° C. for 24 hours. The reaction mixture was cooled to 0° C. and filtered. The vial and solids were washed with water (1 mL). The solids were dried to give cyclocreatine 2 (0.655 g, 58% yield).

Example 5

Preparation and Isolation of [(2-Aminoethyl)Amino]Acetic Acid (3)

A 250 mL, 3 neck flask, equipped with a mechanical stirrer, stopper, and septum, was charged with ethylenediamine (EDA, 67 mL, 1003 mmol). A 30 mL syringe was charged with a solution of chloroacetic acid (CSA, 9.48 g, 100.3 mmol) in DMSO (total volume was 26 mL). The syringe was placed onto a syringe pump set to deliver 3.3 mL/h (total addition time was 8 h). The syringe needle was inserted into the flask via the septum and placed below the level of EDA. Addition occurred at ambient temperature. After addition was complete the reaction mixture was stirred for 10 h at ambient temperature. The reaction mixture was concentrated (60° C., ~10 mbar) to 47 g. Toluene (50 mL) was added and the mixture was concentrated in order to azeotrope EDA. More toluene (50 mL) was added and the mixture was concentrated to 41 g. DMSO (30 mL) was added and the mixture was cooled in an ice/water bath for 30 min. The cooling bath was removed and the mixture was stirred at ambient temperature for 30 min. The mixture was filtered. The flask and solids were washed sequentially with DMSO (50 mL), isopropanol (50 mL), and t-butylmethyl ether (50 mL). The solids were dried under vacuum to give 3 as a white powder (8.74 g, 62%). $^1$H NMR (400 MHz, $D_2O$) δ 3.11 (s, 2H), 2.90-2.70 (m, 4H). MS [M+H]$^+$ m/z 119.1.

Example 6

Preparation of Cyclocreatine 2 from Isolated 3

A 250 mL, 3 neck flask, equipped with mechanical stirrer, reflux condenser and stopper, was charged with 3 (8.74 g, 56.5 mmol) and water (10 mL). A solution of cyanamide (4.4 mL, 50 wt % in water) was added and the mixture was heated to 70° C. in an oil bath for 4 h. Heating was discontinued and the mixture was stirred at ambient temperature for 19 h. The mixture was cooled in an ice/water bath and stirred for 2 h. The mixture was filtered and the flask and solids were washed with cold water (5 mL). The solids were dried under high vacuum to give 2 as a white powder (2.88 g, 36%). $^1$H NMR (400 MHz, $D_2O$) δ 3.78 (s, 2H), 3.66-3.60 (m, 2H), 3.57-3.51 (m, 2H). MS [M+H]$^+$ m/z 144.1.

Example 7

Preparation of Cyclic Creatine Analog ((2-iminotetrahydro-pyrimidin-1(2H)-yl)acetic Acid (4)

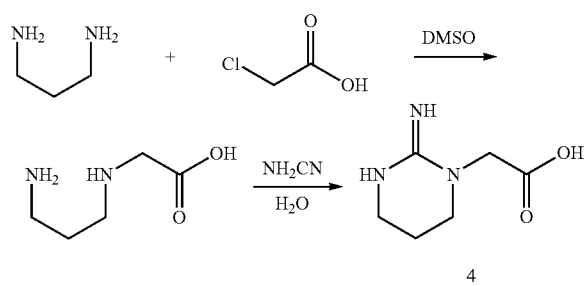

4

A solution of chloroacetic acid (1 equivalent) in DMSO is added to propane-1,3-diamine (10 equivalents) over a period of 8 hours. The reaction mixture is concentrated by vacuum distillation and DMSO is added. The mixture is cooled to 0° C., and then warmed back up to ambient temperature. The resulting slurry is filtered, and the flask and solids are washed sequentially with DMSO, isopropanol, and t-butylmethyl ether. The solids are dried and dissolved into water. Cyanamide (50 wt % solution in water, 1 equivalent) is added and the mixture is heated to 70° C. for 2 h. The reaction is cooled to 0° C. and the resulting slurry is filtered. The flask and solids are washed with water and dried to give 4.

Example 8

Preparation of [(2-Aminoethyl)amino]acetic Acid (3) in DMSO

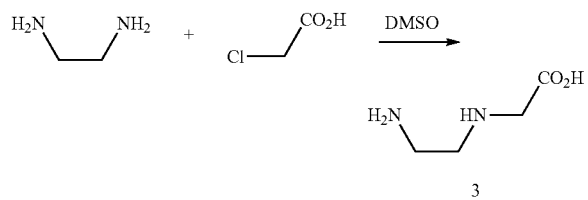

3

A solution of chloroacetic acid was prepared by dissolving chloroacetic acid (500.0 g, 5.29 mol) in DMSO (515.6 g). A 5 L flask, fitted with nitrogen inlet, mechanical stirrer, thermocouple, and peristaltic metering pump was charged with ethylenediamine (3537 mL, 52.9 mol). Cooling with ice water was initiated. The solution in DMSO was then added via a metering pump. Table 1 shows the reaction conditions during addition of chloroacetic acid solution to ethylenediamine:

TABLE 1

Addition of chloroacetic acid solution to EDA

| Entry | Time | Temp. (° C.) | Volume of chloroacetic acid solution remaining |
|---|---|---|---|
| 1 | 10:51 | 17 | — |
| 2 | 11:28 | 18 | — |
| 3 | 12:18 | 16 | 720 |

TABLE 1-continued

Addition of chloroacetic acid solution to EDA

| Entry | Time | Temp. (° C.) | Volume of chloroacetic acid solution remaining |
|---|---|---|---|
| 4 | 13:38 | 11 | 625 |
| 5 | 14:35 | 12 | 550 |
| 6 | 15:17 | 10 | 490 |
| 7 | 16:08 | 8 | 420 |
| 8 | 8:59* | 19 | 0 |

*Time represents the following day.

The reaction mixture was concentrated by rotary evaporation (50-60° C., 14-21 Torr) to remove ethylenediamine. Total amount of distillate collected was 2400 mL. Toluene (900 mL) was added to the residue and the mixture was concentrated by rotary evaporation (60° C., 30 Torr). The residue was transferred to a 5 L flask using DMSO (3 kg). The internal temperature was 28° C. and the mixture appeared cloudy. Cooling (ice/water) was initiated. The reaction mixture was stirred overnight. The resulting suspension was filtered through filter paper. The flask and solids were washed with DMSO (2×500 mL). Solids were washed with isopropanol (2×500 mL) and then washed with tert-butylmethyl ether (2×500 mL). The solids were dried under high vacuum at ambient temperature for 18 hours. Acid 3 was obtained as a white solid (480.4 g, 4.07 mol) in 77% yield.

Example 9

Preparation of Cyclocreatine from 3 and Cyanamide

A 5 liter flask, equipped with nitrogen inlet, reflux condenser, mechanical stirrer, thermocouple, and heating mantle, was charged with compound 3 (478.4 g, 4.05 mol, 1.00 equiv) and deionized water (484.5 g). The resulting slurry was stirred at ambient temperature (22° C.). Cyanamide (50 wt % solution in water, 340.5 g, 4.05 mol, 1.00 equiv) was charged in one portion. The addition of the cold solution caused the internal temperature to drop to 15° C. The reaction mixture was a solution at this point. Heating was initiated. After 22 minutes the internal temperature had risen to 62° C. and eventually rose further to 84° C., at which point heating was stopped. Table 2 shows cyanamide addition:

TABLE 2

Cyanamide addition during Step 2

| Entry | Time | Temp (° C.) |
|---|---|---|
| 1 | 9:28 | 15 |
| 2 | 9:50 | 62 |
| 3 | 9:56 | 70 |
| 4 | 10:01 | 80 |
| 5 | 10:08 | 84 |
| 6 | 11:48 | 71 |
| 7 | 13:05 | 70 |

HPLC/MS showed consumption of 3. Heat was shut off and the reaction was cooled in an ice/water bath. The mixture was then stirred overnight and filtered through filter paper. The flask and solids were washed with deionized water (150 mL). The wet solids were transferred to a 2 L flask, equipped with a mechanical stirrer. Deionized water (450 mL) was added and the thick slurry was stirred at ambient temperature for 3 h. The mixture was filtered through filter paper and the flask and solids were washed with IPA (450 mL). The product was air dried on the filter for 1 h then dried in a vacuum oven (40° C., 25 in Hg, 3 days) to give cyclocreatine as a white solid (248.9 g, 1.74 mol) in 43% yield. The overall yield for the two steps from chloroacetic acid was 33%.

Example 10

Isolation of Intermediate [(2-carbamimidamidoethyl)amino]acetic Acid (A)

A 100 mL round bottom flask, equipped with nitrogen inlet, magnetic stirrer and thermocouple is charged with compound 3 (4.8 g, 4.05 mmol, 1.00 equiv) and deionized water (500 mL). The resulting slurry is stirred at ambient temperature (22° C.) for three days. Cyanamide (50 wt % solution in water, 3.4 g, 4.05 mmol, 1.00 equiv) is charged in one portion. The resultant mixture is stirred for 24 h at room temperature, at which point trifluoroacetic acid is added drop wise with the flask in an ice bath until the pH of the water is 2 by pH paper. The mixture is then frozen and lyophilized to afford a white powder consisting primarily of A and cyclocreatine. Portions (~20 mg) of the powder are dissolved in water and injected onto a preparative reverse phase (C18) HPLC system and the peak corresponding to A is isolated and lyophilized to afford A as a white solid as its bis-trifluoroacetate salt. Expected analytical data for Intermediate A: Mass spectrum (positive mode) m/e=161 (M+1). $^1$H NMR (D$_2$O) δ 2.60 (t, 2H, J=6), 3.00 (s, 2H), 3.13 (t, 2H, J=6) ppm.

The invention is further described in the following numbered paragraphs:

1. A process for the preparation of a compound of formula (I):

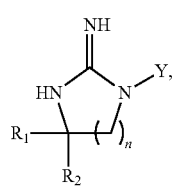

(I)

or a pharmaceutically acceptable salt thereof, comprising the step of reacting a compound of formula (II):

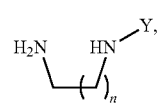

(II)

with a compound of formula (III):

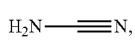

(III)

wherein:
Y is CH$_2$CO$_2$H, CH$_2$CONR$_1$R$_2$ or CH$_2$CO$_2$R$_1$;
R$_1$, R$_2$, independently of each other, is hydrogen, lower alkyl, C$_7$-C$_{12}$ alkyl or lower cycloalkyl; and
n is 1, 2, 3, 4 or 5.

2. The process according to paragraph 1, wherein a carbon within the parentheses in the compound of formula (I) is optionally substituted with R$_3$ and R$_4$, each of which independently of each other is hydrogen, lower alkyl or cycloalkyl.

3. The process according to paragraph 1, wherein n is 1.

4. The process according to paragraph 1, wherein the compound of formula (I) is cyclocreatine or a pharmaceutically acceptable salt thereof.

5. The process according to paragraph 2, wherein said compound is a compound of formula (Ia):

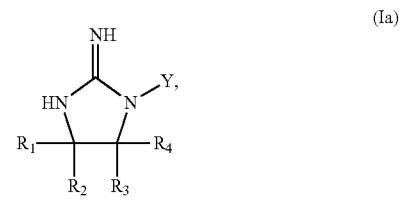

(Ia)

wherein:
Y is CH$_2$CO$_2$H, CH$_2$CONR$_1$R$_2$ or CH$_2$CO$_2$R$_1$;
R$_1$, R$_2$, R$_3$, R$_4$, independently of each other, is hydrogen, lower alkyl, C$_7$-C$_{12}$ alkyl or cycloalkyl,
or a pharmaceutically acceptable salt thereof.

6. The process according to paragraph 1, further comprising a precursor step of reacting ethylenediamine with chloroacetic acid to produce said compound of formula (II).

7. The process according to paragraph 6, wherein the concentration of cyanamide is 1-20 molar equivalents relative to a molar charge of said chloroacetic acid.

8. A compound, selected from the group consisting of:

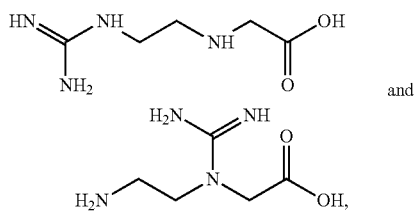

and or a pharmaceutically acceptable salt thereof.

9. A process for making a compound of formula (A):

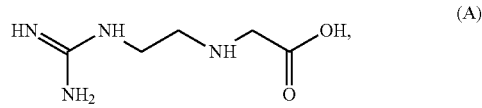 [SMILES: N=C(N)NCCNCC(=O)O]

(A)

comprising the steps of:
reacting a compound of formula 3:

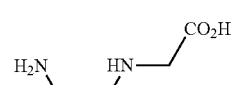

3 with a compound of formula (III):

(III)

10. A process for making cyclocreatine or a pharmaceutically acceptable salt thereof, comprising the step of reacting a compound of formula (A):

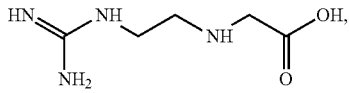
(A)

with a compound of formula (II):

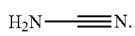
(III)

11. A process for making cyclocreatine or a pharmaceutically acceptable salt thereof; comprising the step of reacting a compound of formula (B):

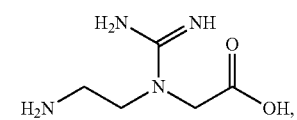
(B)

with a compound of formula (III):

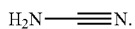
(III)

12. Cyclocreatine, or a pharmaceutically acceptable salt thereof, prepared by a process comprising the step of reacting a compound of formula (A):

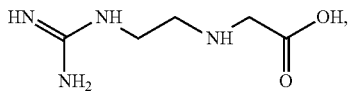
(A)

or a compound of formula (B):

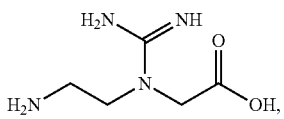
(B)

with a compound of formula (III):

(III)

It is to be understood that the invention is not limited to the particular embodiments of the invention described above, as variations of the particular embodiments may be made and still fall within the scope of the appended claims.

The invention claimed is:

1. The compound

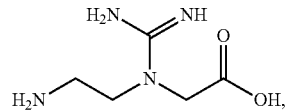

or a pharmaceutically acceptable salt thereof.

2. A process for making cyclocreatine or a pharmaceutically acceptable salt thereof comprising the step of reacting a compound of formula (B):

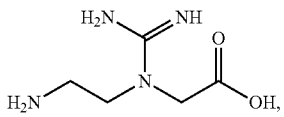
(B)

with a compound of formula (III):

 (III).

* * * * *